United States Patent [19]

Leigh et al.

[11] Patent Number: 5,172,702
[45] Date of Patent: Dec. 22, 1992

[54] DISPOSABLE SPRING-LOADED SOFT TISSUE BIOPSY APPARATUS

[75] Inventors: Harold G. Leigh, St. Louis, Mo.; David L. O'Dell, Mishawaka; Hugh A. Bourassa, Granger, both of Ind.

[73] Assignee: Medical Device Technologies, Inc., Gainesville, Fla.

[21] Appl. No.: 678,724

[22] Filed: Apr. 1, 1991

Related U.S. Application Data

[63] Continuation of Ser. No. 440,647, Nov. 24, 1989, Pat. No. 5,036,860.

[51] Int. Cl.$^5$ ............................................. A61B 10/00
[52] U.S. Cl. ................................. 128/754; 606/171
[58] Field of Search .................... 128/749, 751–754; 606/107, 170, 171

[56] References Cited

U.S. PATENT DOCUMENTS

| | | | |
|---|---|---|---|
| 4,243,048 | 1/1981 | Griffin | 128/754 |
| 4,881,551 | 11/1989 | Taylor | 128/754 |
| 4,944,308 | 7/1990 | Akerfeldt | 128/751 |

Primary Examiner—Randy C. Shay
Attorney, Agent, or Firm—Emrich & Dithmar

[57] ABSTRACT

Soft tissue biopsy apparatus (10) for obtaining a tissue specimen. An elongate housing (12) has an opening (20) at one end (14). A hollow cannula (26) is positioned within the housing, is reciprocally movable therewithin, and one end (28) of the needle extends through the opening for insertion into tissue (T) from which a specimen is to be taken. A needle (44) is positioned within the cannula, is reciprocally movable therewithin, and also has an end (46) extending through the opening for insertion into the tissue. This needle has a recess (50) adjacent its outer end in which a tissue specimen is captured. The needle is connected to a slide (68) by which the needle is moved independently of the cannula. A sleeve (110) installed over the housing is manually operable to move the slide to a selected and cocked position prior to insertion of the cannula/needle into the tissue. Movement of the slide moves the second needle from a first position to a second position while the cannula remains stationary. A release mechanism (114) operable by the user after the insertion of the assembly into the tissue initially returns the needle to its first position and then moves the cannula from a first position to a second position. Movement of the cannula to its second position causes the end of the said cannula to cover the end of the needle to capture the tissues specimen within the recess.

9 Claims, 5 Drawing Sheets

DISPOSABLE SPRING-LOADED SOFT TISSUE BIOPSY APPARATUS

This is a continuation of application Ser. No. 07/440,647, now U.S. Pat. No. 5,030,860 filed Nov. 24, 1989.

BACKGROUND OF THE INVENTION

This invention relates generally to a biopsy apparatus and more specifically pertains to a disposable biopsy apparatus for performing a soft tissue biopsy.

It has been noted that biopsies or sampling of the inner tissue of animals and humans has become increasingly common. While there are a number of ways in which biopsies are performed, one method involves the use of two needles. One of these is a cannula or hollow needle; and the other is a stylet or needle having a recess along a portion of its length usually just behind the tip of the needle. In practice, the stylet is positioned within the cannula and the relative movements of the two needles co-ordinated to extract a tissue specimen. Thus, when the subject's skin is punctured, the recess portion of the stylet is enclosed within the cannula. Once the needles are moved to within proximity of the site from which the specimen is to be taken, the stylet is moved relative to the cannula so the recess is exposed and filled with specimen tissue. Then, the cannula is moved relative to the stylet so the cannula overcovers the recess and captures the tissue specimen. The stylet and cannula are then withdrawn, the cannula being maintained in its position covering the recess during extraction. Afterward, the cannula is pulled back from the stylet, exposing the recess, and allowing the captured tissue sample to be removed to a specimen container, or the like, for testing. The early patent to Griffith, U.S. Pat. No. 3,477,423, shows this obturator-sheath relationship.

A number of biopsy implements are known by which the above described procedure is accomplished. One such device is disclosed in the U.S. Pat. No. 4,667,684 which was invented by one of the same inventors of the present application. The device of this invention features a stylet and a cannula which are fixed at their ends to respective hubs. Both hubs are located in a guideway in the upper end of a pistol grip style hand gripping device. The device is designed for single-handed usage wherein pressing on a trigger mechanism housed in the grip results in a sequential movement of the stylet and cannula to secure a tissue specimen. A second type of implement is shown, for example, in U.S. Pat. No. 4,699,154. This device employs a series of slides and springs positioned within a box-shaped housing. A hook latch and push button release mechanism generally at the end of the device, are employed to move the stylet and cannula assemblies within the device to obtain the tissue specimen. It appears to operate just the opposite from the current invention, and incorporates dual slide bars to achieve its functioning.

While both of the biopsy devices described above, as well as others known in the art, function for their intended purpose of obtaining a biopsy sample, recent medical epidemics have imposed on the medical profession certain cautionary measures which did not have to be dealt with in the past. Of particular importance is limiting the use of needles to only one individual and, at the same time, protecting the user of the biopsy device from inadvertent exposure to potentially deadly infections. Typically this means that the biopsy device is limited to a single usage and then safely discarded. Given the number of biopsies currently being performed, there is a need for a low-cost, simple to use (preferably by one person using only one hand), instrument, which cannot accidently injure either the patient or the user, and which can readily and safely be discarded after application.

Other patents relating to this technology include the U.S. Pat. No. 4,570,632 to Woods, pertaining to a device in the category of cystotome for use in eye surgery. The U.S. Pat. No. 4,476,864, to Tesel, shows a multiple punching device for use in hair transplant. The U.S. Pat. No. 4,600,014, to Beraha, shows a transrectal prostate biopsy device and method. An application filed under No. A61B 10/00, under the PCT, shows a device for taking tissue sample. Another PCT application published under No. A61M 25/00, shows a wire-guide intended to be inserted into body ducts. A Soviet Union patent No. 175,611, shows an instrument for achieving puncture biopsy. A European Patent Office patent No. 0010321, shows another form of biopsy device capable of being operated with one hand. Finally, what appears to be an Austrian patent No. 141,108, shows another form of endoscopic sample excision instrument.

SUMMARY OF THE INVENTION

It is a primary object of the present invention to provide a fully automated, structured biopsy apparatus for obtaining biopsy specimens from soft tissue such as human flesh.

It is also an object of the invention to provide such a biopsy apparatus which can be used single-handedly by a physician or medical technician, is very light weight in construction, and is easily manipulated by the user for insertion into the region of a body from which a specimen is to be taken.

It is another object of the invention to provide a biopsy apparatus employing a simple, single triggering mechanism, which is selective in the quantity of specimen obtained, to initially and promptly collect a tissue specimen within the recess of an extending needle or stylet and simultaneously thereafter overcover the specimen with a hollow needle or cannula.

It is yet another object of the invention to provide an apparatus which is disposable after the apparatus is withdrawn from the body and the specimen extracted from the recess thus to prevent usage of the same needle with more than one individual.

And, a further object of the invention is to provide a low-cost biopsy apparatus which is compact in size and light-weight, and which can be safely used by the physician or technician.

Briefly stated, a soft tissue biopsy apparatus of the present invention is for obtaining a tissue specimen, generally from within the region where a suspected maglignancy may be present. An elongate housing has an opening at one end. A first and hollow cannula is positioned within the housing and is reciprocally movable therewithin. One end of the cannula extends through the opening for insertion into tissue from which a specimen is to be taken. A needle is positioned within the first cannula and is reciprocally movable therewithin. The needle also has an end extending through the opening for insertion into the tissue. This needle has a notch or recess adjacent this end in which a tissue specimen is capturable The needle is mounted in a slide which allows this needle to move independently of the first cannula. The slide is manually cocked by a user of the apparatus. This action moves the slide to a selected position prior to insertion of the combined cannula and needle into the tissue. Movement of the slide moves the cannula and needle from a first position to a second position. A release mechanism, operable by the user through exertion of only two fingers of the same hand holding the device, and after insertion of the device into the tissue, initially returns the needle to its first position and then moves the cannula to its proximate first position. Movement of the cannula to this position causes its outer end to cover the recessed specimen of the needle whereby the tissue specimen is captured by the needle within the cannula.

There are many other unique features about this invention that make it rather facile of manufacture and assembly, unique in usage and application, and which provides efficient results for each biopsy taken, before it is readily disposable after a single usage, or repeat usage upon the same patient.

The entire device is fabricated with generally concentrically arranged parts and components. For example, the relationship between the cannula and needle, as they are concentrically arranged with respect to each other, provides for axial alignment of the various means that provides for the thrust of, initially, the needle forwardly, once inserted within proximity of the specimen being tested, and then provides for capture of the needle recessed specimen by means of overlying coverage through the concentrically arranged cannula. Furthermore, the relationship between the depth of penetration, and coverage, of the needle, by the cannula, can be controlled by a spacer means that limits the extent of forward movement of the needle, relative to the cannula, during its specimen accepting manipulation. Also, the device can be cocked to different settings to control depth of penetration, and the strength of force of the forward movement of the needle and its cannula. Furthermore, this invention provides means for initiating the triggering of its actuation, quite distinct from those shown in the prior art, which usually require the initiation of a trigger mechanism, normally located and disposed at the back of any biopsy device, requiring the assistance of the second hand of the technician, whereas, in the current invention, the triggering means is acceptably located at the position of the same hand of the medical technician who has just inserted the device, and can immediately utilize an index and one other finger, of the same hand, for initiating a biopsy sample taking activity. Thus, this device is truly for a single handed operation, to provide an effective specimen of a biopsy for ready analysis by the medical personnel.

Other objects and features of this invention will become more apparent to those skilled in the art upon reviewing the summa of the invention herein, in combination with a study of the description of the preferred embodiment, with respect to its drawings.

BRIEF DESCRIPTION OF THE DRAWINGS

FIGS. 5a and 5b are respective side and front elevational views of a slide for moving the stylet and cannula assemblies;

FIGS. 6a-6d are elevational views of the housing taken at respective quarter-turns of the said housing;

FIG. 7 is a sectional view taken along line 7—7 in FIG. 6a;

FIG. 9 is a sectional view taken along line 9—9 in FIG. 8; and

FIGS. 10-13 are sectional views of the apparatus illustrating the sequence of operations performed in obtaining a biopsy sample through usage of the apparatus.

Corresponding reference characters indicate corresponding parts throughout the drawings.

DESCRIPTION OF A PREFERRED EMBODIMENT

Referring to the drawings, a soft tissue biopsy apparatus of the present invention is indicated generally at 10. Apparatus 10 is a hand-held implement for use by a doctor or medical technician to obtain a tissue sample and specimen from a patient for laboratory testing. Its primary use therefore is as an aid in diagnosis. It is a feature of the apparatus that it be a light-weight, generally less than one and one-half ounces in weight, safely disposable, easy to use implement that can be readily adjusted so a biopsy sample can be taken from any part of the body whether near the skin's surface or deeper within the body, so that the specimen from the suspected region can be tested and analyzed.

The apparatus includes an elongate housing 12 having a tapered front end 14, a hollow, cylindric body section 16, and an open back end 18 which is internally threaded proximate its back end. An opening 20 is formed in the front end of the housing, and a threaded cap 22 threadedly fits into the open, rear end of the housing. The housing is made of a light-weight polymer material and the length of the housing is such as to comfortably fit in one hand of the doctor or technician employing the apparatus.

A first and hollow cannula means 24 is positioned within housing 12. As particularly shown in FIGS. 3a and 3b, means 24 comprises a cannula assembly including a hollow needle or cannula 26 the tip end 28 of which extends through opening 20 for insertion into tissue from which a specimen is to be taken. The other end 30 of the cannula is affixed to a circular pedestal 32. The pedestal has an upstanding, circular support 34 into which end 30 of the cannula tightly inserts. This support projects outwardly from the forward face of the pedestal. An integral extension of the needle 36 extends rearwardly through and to the rear face of the pedestal, as can be seen. The pedestal, support, and extension all have a longitudinal bore which is of uniform diameter and concentric with the longitudinal bore 38 formed through the cannula providing an opening from end 28 of the cannula, and internally along its entire length. A spring 40 is insertable into the housing. The spring tapers to conform to the gradually tapering internal diameter of the housing at its forward end so the front end of the spring seats against the interior nose of the housing. Although, springs of other shapes may likewise be used. The rear end of the spring seats against the front face of the pedestal to bias the cannula assembly toward the rear of the housing. As will be described hereinafter, the cannula assembly is reciprocally movable within the housing 10 for cooperating in obtaining the tissue sample.

Figures 1, 3A, 3B, 4A, 4B:
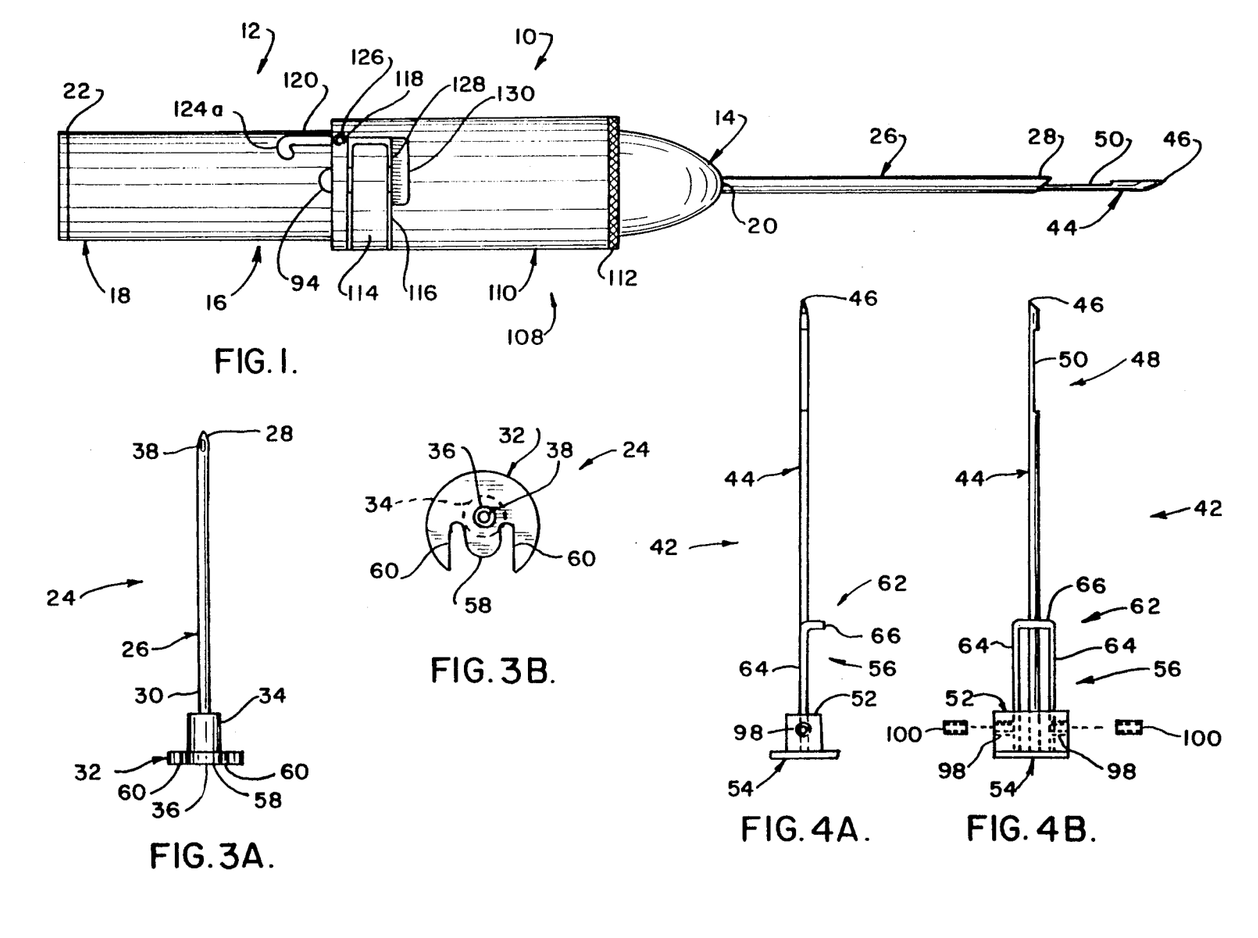
FIG. 1 is an elevational view of a biopsy apparatus of the present invention.
FIGS. 3a and 3b are respective elevational and bottom plan views of a cannula assembly used in the apparatus.
FIGS. 4a and 4b are respective side and front elevational views of a stylet assembly used in the apparatus.
Figure 2:
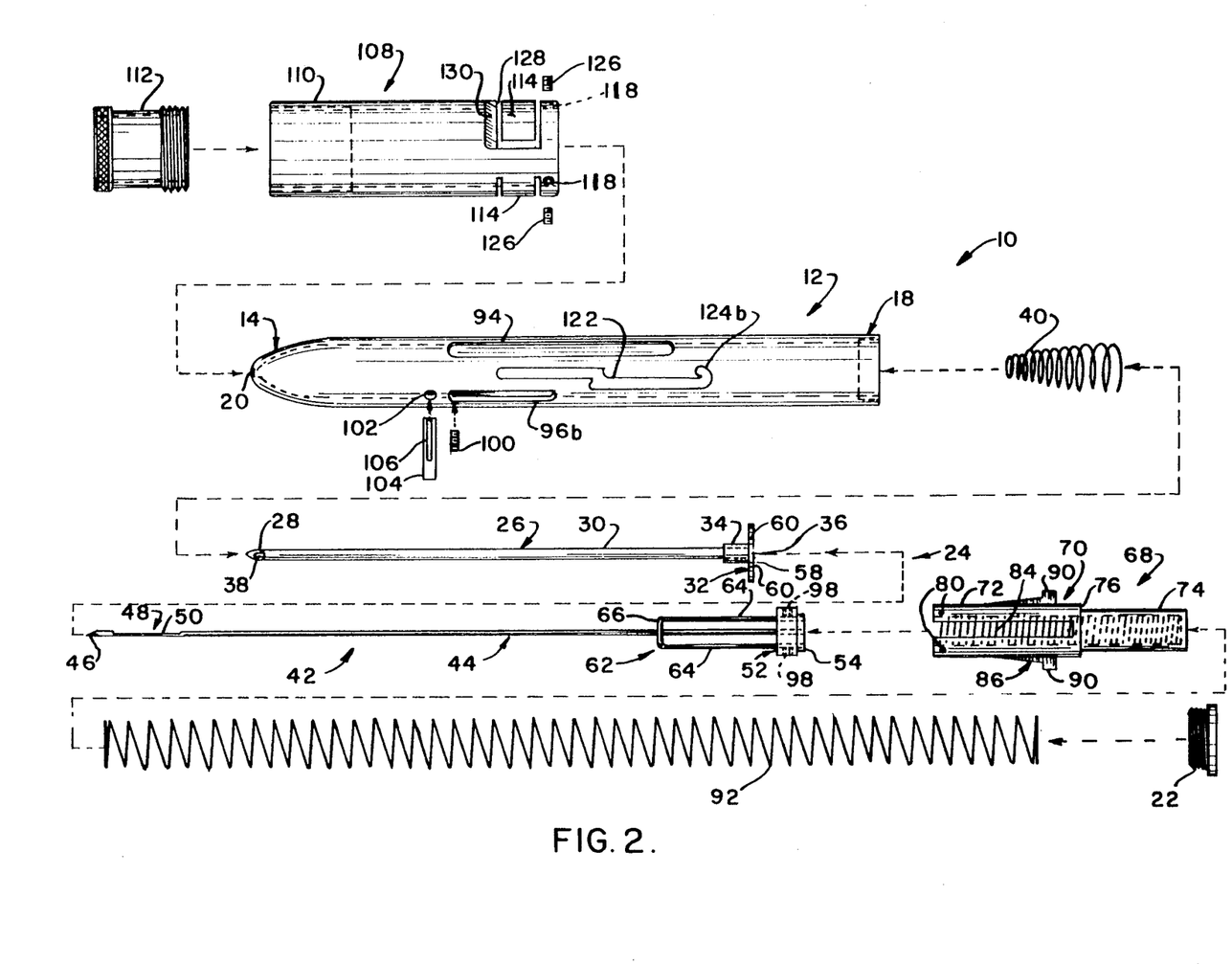
FIG. 2 is an exploded view illustrating the sequence of assembly of the components comprising the apparatus.

A needle means 42 is also installed in the housing 10. As shown in FIG. 2, this needle means is positioned within the first cannula means and is reciprocally movable therewithin. Referring to FIGS. 4a and 4b, this needle means comprises a stylet assembly. The stylet assembly includes a stylet 44 having a tip end 46 for penetration of tissue. A tissue sampling means 48 comprises a recess or notch 50 adjacent end 46 of the stylet, as known in the art. As will be described hereinafter, a tissue specimen is captured in this notch during application of the apparatus. The diameter of stylet 44 is such that the stylet can be slidably inserted within the cannula assembly, through its inner channel and the opening in the end of extension 36. The length of the stylet is such that when so installed, the tip end of the stylet will extend sufficiently far enough through the open end 38 of the cannula that all of the recess is exposed for tissue capturing, or retracted therein for tissue confinement. The other end of the stylet extends through a base 52 and terminates at its pad 54 of the assembly. Pad 54 is a circular pad while base 52 is a rectangular unit which sits atop the pad, the width of the base being greater than to the dimension of the pad, as can be seen.

The stylet assembly includes a means 56 for interlocking the stylet and cannula assemblies and for limiting movement of the stylet relative to the said cannula. Thus, even though the stylet is reciprocally movable within the cannula and independently of the movement of the cannula, the extent of the stylet movement is somewhat restricted. Pedestal 32 has a tongue portion 58 formed by two slots 60 which extend inwardly from the perimeter of the pedestal to respective sides of support 34. The radius of the tongue is less than that of the remaining portion of the pedestal so to create a recessed section about the periphery of the pedestal. Means 56 includes a bail 62 having legs 64 extending from pad 54, through base 52, and parallel to the stylet. The bail is generally U-shaped with the closed end portion turned at a right angle to the longitudinal axis of the bail. Thus, the upper ends of the legs are turned to form a lip 66 which fits over tongue 58 of pedestal 32. As a result, the length of travel of the stylet corresponds to the length of the legs of the bail beyond the upper end of the base. It should be obvious that other forms of bail, such as one formed of a polymer, can be envisioned for usage herein.

Figures 5A, 5B, 7, 9:
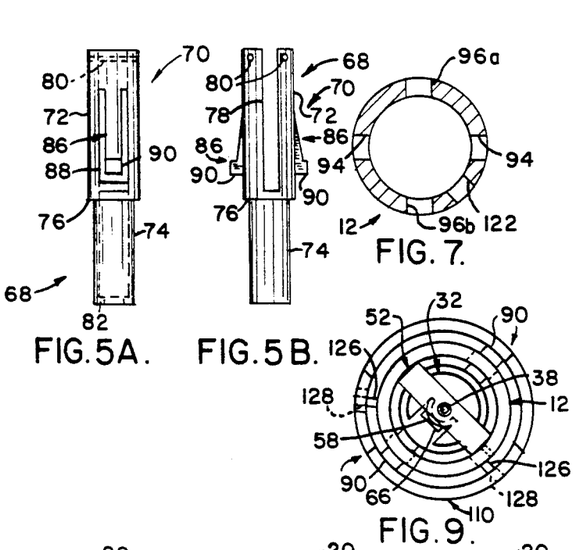

Next, apparatus 10 includes a slide means 68 to which the stylet assembly is connected for moving the stylet assembly independently of the cannula assembly. Referring to FIGS. 5a and 5b, the slide means includes a cylindrical, hollow tube 70 having a first section 72 and a second section 74. The inner diameter of the tube is uniform along its length and corresponds to the diameter of pad 54. However, the outer diameter of section 72 is greater than that of section 74 so as to create a shoulder 76 at the junction between the two sections. Further, the outer diameter of section 72 corresponds to the width of base 52.

Section 72, which is the forward of the two sections when the slide is installed in the housing, has a pair of opposed longitudinal slots 78 which extend rearwardly from the forward end of the section almost to the junction between the sections. Base 52 and pad 54 are inserted into the open, front end of the housing, the respective sides of the base being positioned in the slots. A pair of pins 80 extend transversely of section 72 on both sides of the slots. The pins are inserted after the base/pad combination is installed with the pins being between the outer surface of the pad and the front end of the slide. The pins thus hold the base/pad combination in the slide. Further, a circumferential inwardly directed lip 82 is formed about the opening at the rear of section 74. A spring 84 inserts within the tube 70, and seats against this lip and bears against the backside of connected pad 54, urging the pad forwardly against the restraining force exerted by the pins.

Slide means 68 also includes a pair of flexible fingers 86 formed in section 72 of tube 70. The fingers are formed on opposite sides of the section and are each arranged at a quarter-turn from the slots 78. Each finger is formed by a U-shaped channel 88 through the sidewall of section 72, the sides of the channel extending generally longitudinally of the tube from near a forward end thereof, and the proximate base of the channel being slightly forwardly of the inner end of the slots. The fingers thus extend in a rearward direction of the tube. Further, each finger has an outwardly projecting tab 90 at its distal end, as can be seen. Finally, a spring 92 bears against shoulder 76 of the slide, when it is installed in housing 12, to urge the entire slide assembly forwardly. This spring seats against the inward end of cap 22 which, as previously noted, is threadably received in the back end of the housing, with this spring 92 being disposed within the proximate opening, provided within the housing 12.

As thus far described, the base/pad combination of the stylet assembly is installed in section 72 of tube 70 with spring 84 urging the stylet assembly forwardly. This spring 84 has equivalent or slightly greater strength than the spring 40. Although, other relative spring strengths can be utilized. Tip 46 of stylet 44 is inserted into the open end cannula extension 36 of the cannula assembly and pushed forward until the end of the extension strikes the outer end of base 52. Tip 46 of the stylet extends through the opening in the tip end 28 of the cannula when the insertion step is complete. The outer end of bail 62 is hooked over tongue 58 on the cannula assembly pedestal to interlock the two assemblies together. Although, other forms of engagement of these components relative to each other may be utilized. Spring 40 is inserted into the back end of the housing and the combined cannula/stylet assemblies, tip ends first, are next inserted. The tip ends project through opening 20 at the front end of the housing when the insertion is complete. Housing 12 has a pair of opposed longitudinal guide slots 94 formed intermediate its length and the projecting tab portion of the fingers 90 fit in the respective slots.

In addition to the slots 94, a pair of base guide slots 96a, 96b are also formed in the sidewall of the housing. These slots, which are also longitudinal slots are formed to guide movement of the stylet assembly base. For this purpose, threaded bores 98 extend inwardly into the base from its respective outer sides. When the slide or tube 70 is properly installed with the tabs 90 extending through the slots 94, the bores in the sides of the base are aligned with the slots 96. Pins 100 are then inserted through the slots and into the bores. The pins extend out beyond the sidewall of the housing when installed and so limit movement of the slide with respect to the length of the slots 96 occurs. Also, a circular opening 102 is formed in the sidewall of the housing immediately forward of the forward end of the respective slots 96a. A slotted pin 104 is insertable through one of the openings and extends across the housing, transverse to the stylet and cannula assemblies, and through the corresponding opening on the opposite side of the housing. Pin 104 has a longitudinal slot 106 in which is received the legs 64 of bail 62. The width of the slot is less than the width of the base 52 of the stylet assembly so to act as a stop to forward movement of the assembly. At the same time, the diameter of the pin is less than the width of the slots 78 formed in section 72 of the slide. And, the ends of the pin are immediately forward of the outer ends of the slots and aligned therewith. Thus, while the pin acts as a stop to forward movement of the stylet assembly, it does not inhibit forward movement of the slide.

Apparatus 10 next includes cocking means 108 manually operable by a user of the apparatus for moving the slide to a selected position prior to insertion of combined cannula-stylet 26 and 44 into the tissue. Means 108 comprises a hollow, cylindric sleeve 110 the inner diameter of which is slightly greater than the outer diameter of housing 12 for the sleeve to fit over the housing. The front end of the sleeve is threaded for a spacer 112 to be threaded onto the sleeve. The spacer varies the overall length of the sleeve and likewise can regulate the depth to which the stylet with respect to the cannula can be inserted into the tissue from which a specimen is to be taken. The sleeve is slidingly installed over housing 12. This spacer as threaded onto the sleeve provides an adjustment to the extent of projection of the stylet 44 out of the cannula 26, and therefore limits the amount of recess exposed and the amount of specimen obtained, because the inner threaded end of the sleeve can be contacted by the pins 100 to limit the forward movement of the stylet relative to the forward tip 28 of the cannula. Thus, the extent of exposure of recess 50 can be regulated, to limit the quantity of biopsy obtained.

Figure 6A:
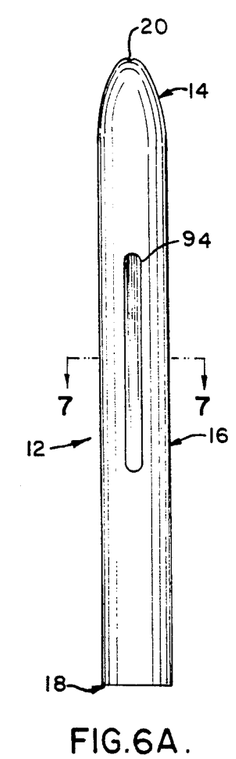
Figure 6B:
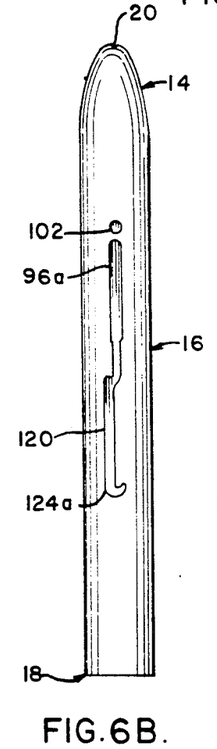
Figure 6C:
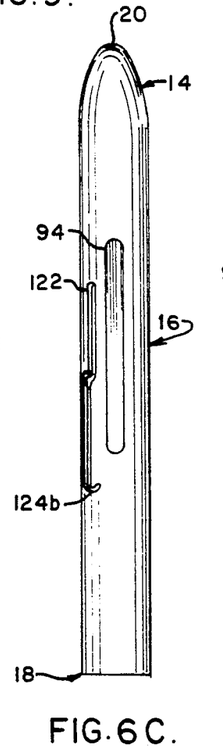
Figure 6D:
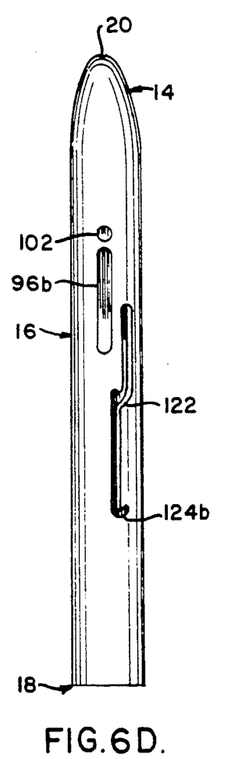
Figure 8:
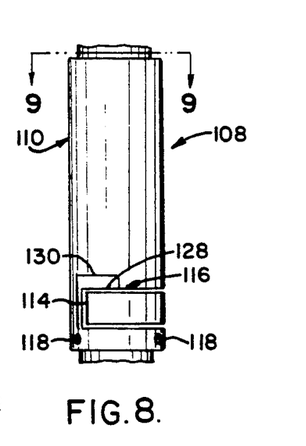
FIG. 8 is an elevational view of a sleeve fitting over the housing and used to initiate operation of the apparatus.

A pair of opposed, flexible tabs 114, comprising pushbutton like members are formed in the sidewall of the sleeve at the proximate rear end thereof. The tabs are each integrally formed with the sleeve and each is formed by a U-shaped channel 116 through the sidewall. The sides of the channel extend circumferentially about the sleeve, and the base of the channel extends longitudinally thereof. The tabs thus extend circumferentially about the sleeve, and are resilient in structure. Intermediate the tabs and the back end of the sleeve are a pair of threaded location holes 118. Housing 12 includes a pair of elongate, longitudinal slots 120 and 122 (See FIGS. 6b–6d). Slot 120 is slightly offset from slot 96a with the forward end of slot 120 communicating with the back end of slot 96b. Slot 122 is positioned intermediate one of the slots 94 and slot 96b. Slot 122 has a reverse S-shape as does the combined slot formed by slots 96a and 120. At the rearward end of the slots is a nose section 124a, 124b respectively. After sleeve 110 is slipped over housing 12, guide pins 126 are threaded into holes 118. When installed, the outer end of the pins are flush with the outer surface of the sleeve, but the inner end of the pins are inserted in the respective slots 120, 122 to guide movement of the sleeve during cocking of the apparatus. Also, as noted, these pins may provide for a half cocking of the sleeve upon the housing by locating said pins at the S-shaped curve, and the recesses thereat, so as to allow the device to trigger at an approximate one-half strength, and move an approximate half stroke.

The outer end of each tab 114 is immediately adjacent projecting tab portion 90 of each finger 86 in slide means 68. This projection extends sufficiently far past the outer surface of housing 12 that a lip 128 formed by the forward leg within the channel 116 contacts the tab as the sleeve is moved rearwardly over the housing. The force of the lip against the finger, as the sleeve moves, draws slide tube 70 rearwardly and moves stylet assembly 42 from a first position (see FIG. 10) to a second position (see FIG. 11). Thereafter, when the user simultaneously presses in on the end of both tabs 114, the fingers are pushed into the housing, which releases the slide to return to its original position. A clearance section 130 of the sleeve immediately adjacent the lips 128 adjacent the free end of the tabs 114, provides for greater depressing of the tab during triggering of the apparatus.

Figure 10:
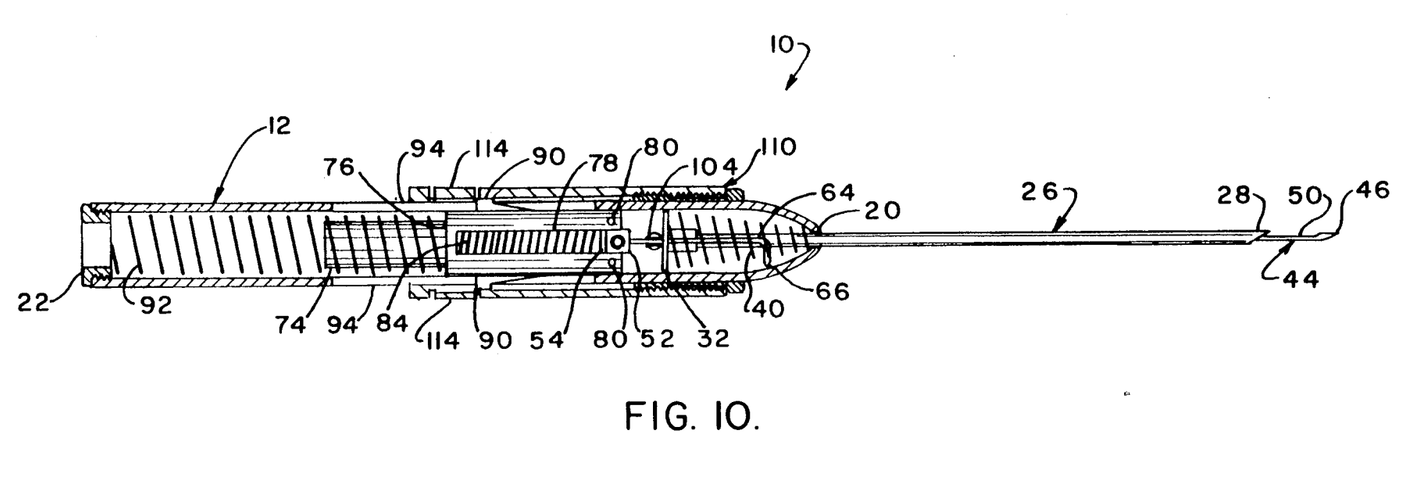
Figure 11:
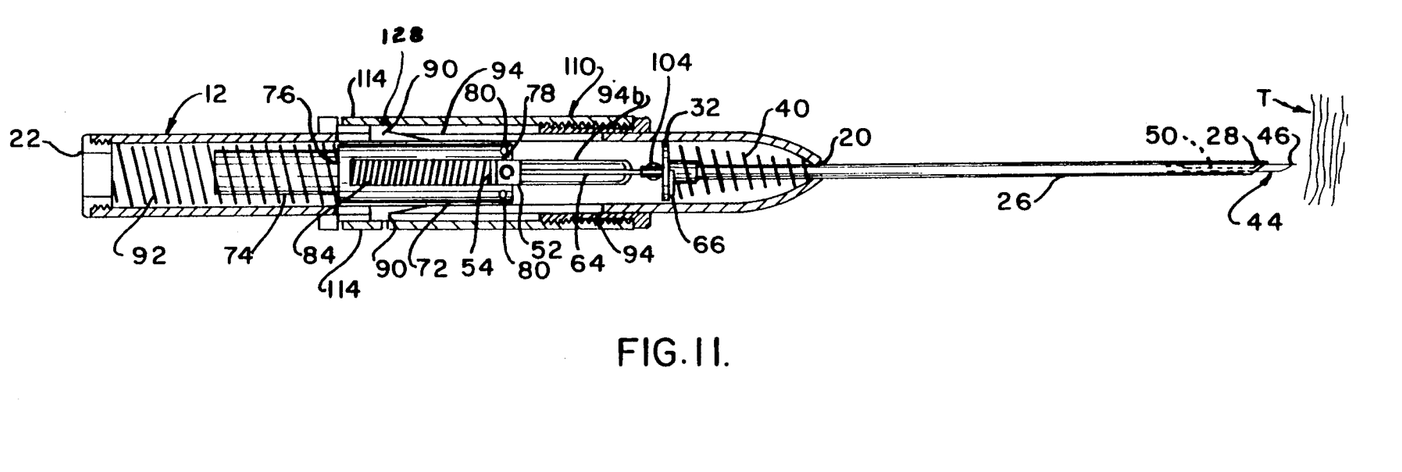

Operation of apparatus 10 to obtain a tissue specimen is best understood with reference to FIGS. 10–13. As shown in FIG. 10, the relationship of the stylet recess relative to the cannula can be seen. Prior to use, through, and before cocking, the stylet is normally retracted within the cannula in the working relationship as shown in FIG. 11. During working, spring 92 bears against shoulder 76 and urges slide 70 forwardly (to the right). Pin 104, acting as a stop, limits movement of the slide. Spring 40 bearing against the forward face of pedestal 32 urges cannula assembly 24 rearwardly (to the left). The tip end of the stylet extends only slightly beyond the tip end of the cannula at this time. Sleeve 110 is also at a forward position and te pins 126 are at a midpoint along the length of their respective slots 120, 122. Fingers 90 extend out past the sides of the housing at a point to the rear (left) of the lips 114 of the sleeve.

Prior to inserting the tip end of the apparatus into the tissue, the user grasps the sleeve and draws it rearwardly (to the left) to cock the apparatus. As the sleeve moves, the lips 128 contact the extended fingers 90 and the sleeve pulls slide tube 70 rearwardly, compressing the strong spring 92. Pins 80, bearing against the pad 54 of the stylet assembly, force the stylet assembly to the rear of the housing as the slide moves. Movement of the slide is stopped when the pins 100 extending from the sides of base 52 reach the rearward end of the respective slots 96a, 96b. At this time, the pins 126 extending inwardly from sleeve 110 reach the rearward end of their respective slots 120, 122. On the other hand, half cocking can be done by positioning the pins 126 at the S-curve recesses. By now, with a slight turning of the sleeve, the user can set the pins 126 into the recesses or nose sections 124a, 124b of the slots to lock the sleeve and the apparatus in a cocked position. The sleeve will remain as cocked because of the force of spring 92 on slide means 68. The tip end of the stylet is now substantially withdrawn into and aligned with he tip end of the cannula. Further, the tips of the stylet and cannula remain relatively close together as shown in FIG. 11, which facilitates the insertion of them into the tissue T from which the biopsy sample is being taken.

Figure 12:
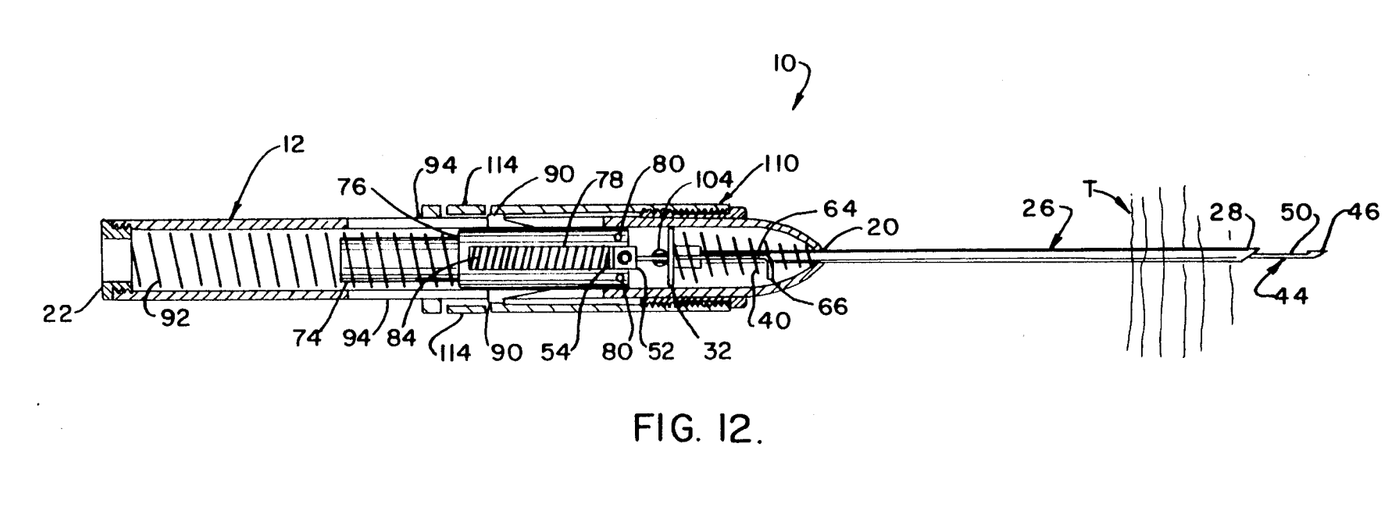
Figure 13:
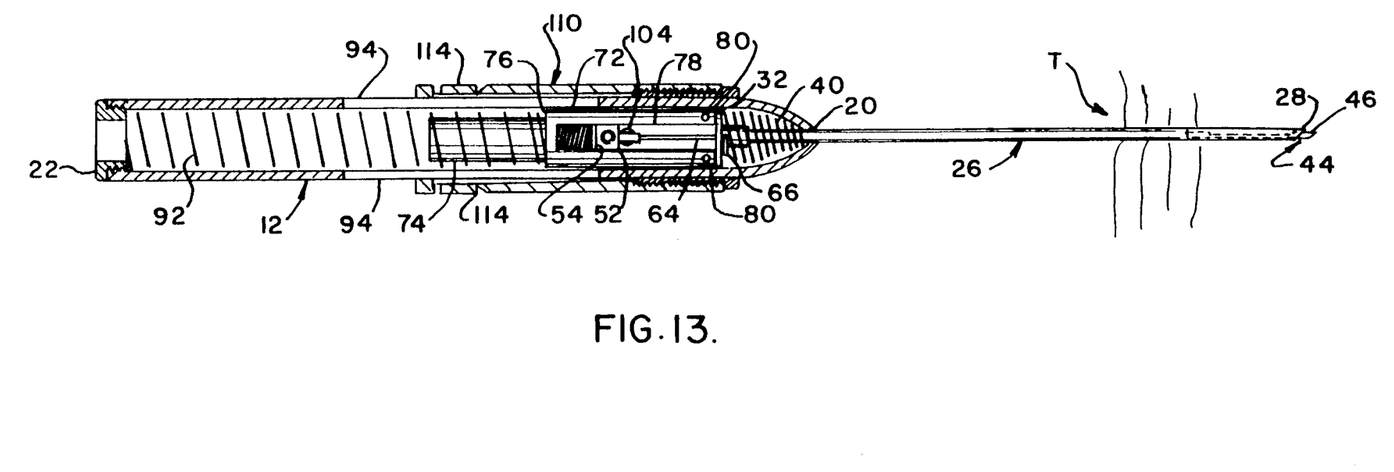

After insertion of the apparatus within the skin, the user moves the housing about until they have the tip ends of the apparatus positioned in proximity with the tumor or portion of the body to be specimened. During this time, the sleeve is maintained in its cocked and locked position, as aforesaid. When the user is satisfied the apparatus is properly positioned, he simultaneously presses inward on both the tabs 114. This action pushes the the tabs 90 of fingers 86 inwardly and away from the lips 128 of the sleeve which have held them in place. Spring 92 now propels slide means 68 forwardly, driving the slide 70 toward the nose end of the housing. As shown in FIG. 12, the stylet assembly is also driven forwardly, with additional pressure from the spring 84, with the tip end of the stylet moving deeper into the tissue. The notch in the stylet is now exposed to the degree allowed by the spacer 112, and tissue fills the recess 50. Forward movement of the slide is abruptly halted when base 52 of the stylet assembly contacts pin 104, and the spring 40 acting as a buffer.

During the interval in which the stylet assembly is moved from its retracted to its extended position, the cannula assembly remains reasonably stationary. Now, however, the forward end of tube 70 strikes the rear face of pedestal 32 and, under the continued urging of spring 92, the cannula assembly is driven forward. The outer end of the cannula now overcovers or shrouds recess 50 in the stylet capturing a tissue sample within the notch. See FIG. 13. The forward movement of the cannula assembly is halted by the forward face of the pedestal 32 striking lip 66 of bail 62.

During the above described latter movement, both spring 84 within slide 70, and spring 40 at the forward end of the housing, are compressed, the latter acting as a buffer. Both springs now move to restore themselves to their original positions. In doing so, they push the slide means 68 and the cannula assembly rearwardly in housing 12. This action serves to simultaneously help withdraw both the stylet and cannula assemblies from the tissue sampling site. The user now pulls on the housing to extract the cannula and stylet from the tissue. The apparatus can then be taken to a laboratory or testing facility at which the tissue sample is removed from the notch for testing. The apparatus can then be discarded.

Variations or modifications to the structure of this invention, as described, in addition to its method of operation, may occur to those skilled in the art upon reviewing the definition of the invention herein. Such variations or modifications, if within the spirit of this invention, are intended to be encompassed within the scope of any claims to patent protection issuing upon this development. The description of the preferred embodiment set forth herein is done so for illustrative purposes only.

Having thus described the invention, what is claimed and desired to be secured by Letters Patent is:

1. A soft tissue biopsy apparatus for obtaining a tissue specimen comprising: an elongate housing having a forward end and a rearward end, said housing having an opening at said forward end; a hollow cannula means positioned within said housing and reciprocally movable therewith, said cannula means having a distal end extending through said opening for insertion into tissue from which a specimen is to be taken; needle means mounted concentrically with respect to said cannula means to extend therethrough and reciprocally movable therewithin, said needle means having a distal end extending through said opening for insertion into the tissue and sapling means adjacent said distal end in which a tissue specimen is capturable; biasing means operatively coupled to said needle means near said proximal end of said needle means to urge said needle means toward said forward end of said housing; resilient means operatively associated with said needle means and said cannula means urging said needle means and said cannula means to respective at rest positions; cocking means associated with said needle means for manually moving said needle means against the force of said biasing means to a predetermined selected position prior to insertion of said distal ends of said cannula means and said needle means into the tissue; releasing means associated with said needle means for initially enabling said needle means to move from said predetermined selected position to a sampling position under the force of said biasing means, whereby said needle means compresses said resilient means and for then moving said cannula means relative to said needle means to a position whereat said distal end of said cannula means covers said sampling means of said needle means to capture the tissue specimen in said sampling means of said needle means, said resilient means restoring said needle means and said cannula means to their at rest positions after the tissue specimen has been captured in said sampling means of said needle means.

2. The apparatus of claim 1, wherein said resilient means comprises first resilient means operatively coupled to said needle means and second resilient means operatively coupled to said cannula means.

3. The apparatus of claim 2 wherein said first resilient means comprises a first spring which is compressed in response to movement of said needle means to said sampling position; and said second resilient means comprises a second spring which is compressed in response to movement of said cannula means to said sampling position.

4. The apparatus of claim 1, wherein said biasing means comprises a spring which is compressed in response to rearward movement of said needle means.

5. The apparatus of claim 1, wherein said needle means includes a stylet having said sampling means at the distal end thereof and slide means constructed and arranged for reciprocating movement within said housing, said stylet being supported by said slide means and movable therewith, and said slide means including means adapted to engage said cannula means as said needle means is moved towards said sampling position for moving said cannula means to said sampling position.

6. The apparatus of claim 1 including means for adjusting the degree of exposure of said sampling means relative to said cannula means when said needle means is released from said predetermined position to move to said sampling position.

7. A soft tissue biopsy apparatus for obtaining a tissue specimen comprising: an elongate housing having a forward end and a rearward end, said housing having an opening at said forward end; a hollow cannula means positioned within said housing and reciprocally movable therewithin, said cannula means having a distal end extending through said opening for insertion into tissue from which a specimen is to be taken; needle means mounted concentrically with respect to said cannula means to extend therethrough and reciprocally movable therewithin, said needle means having a distal end extending through said opening for insertion into the tissue and sampling means adjacent said distal end in which a tissue specimen is capturable; biasing means operatively coupled to said needle means near said proximal end of said needle means to urge said needle means toward said forward end of said housing; first resilient means operatively coupled to said needle means thereby urging said needle means towards an at rest position; second resilient means operatively coupled to said cannula means thereby urging said cannula means towards an at rest position; cocking means associated with said needle means for manually moving said needle means against the force of said biasing means to a predetermined selected position prior to insertion of said distal ends of said cannula means and said needle means into the tissue; releasing means associated with said needle means for enabling said needle means to move from said predetermined selected position to a sampling position under the force of said biasing means, and against the force of said first resilient means and to move said cannula means relative to said needle means and against the force of said second resilient means towards said sampling position, whereby said distal end of said cannula means covers said sampling means of said needle means to capture the tissue specimen in said sampling means of said needle means, said first and second resilient means restoring said needle means and said cannula means respectively, to their at rest positions after the tissue specimen has been captured in said sampling means of said needle means.

8. A soft tissue biopsy apparatus for obtaining a tissue specimen comprising: an elongate housing having a forward end and a rearward end, said housing having an opening at said forward end; a hollow cannula means positioned within said housing and reciprocally movable therewithin, said cannula means having a distal end extending through said opening for insertion into tissue from which a specimen is to be taken; slide means positioned within said housing and reciprocally movable therewithin, needle means operatively associated with said slide means and mounted concentrically with respect to said cannula means to extend therethrough and reciprocally movable therewithin, said needle means having a distal end extending through said opening for insertion into the tissue and sampling means adjacent said distal end in which a tissue specimen is capturable; biasing means operatively coupled to said needle means near its proximal end, urging said needle means toward said forward end of said housing; cocking means including a cylindrical sleeve slidingly installed over said housing, said sleeve defining means adapted to engage said slide means for manually moving said slide means and said needle means rearwardly against the force of said biasing means to a predetermined selected position prior to insertion of said distal ends of said cannula means and said needle means into the tissue, rearward movement of said slide means shifting said needle means from its at rest position to a second position; releasing means associated with said needle means for releasing said slide means and said needle means from said predetermined selected position thereby enabling said needle means to move relative to said cannula means from said predetermined position to a sampling position under the force of said biasing means exposing said sampling means, with said slide means under the force of said biasing means engaging and moving said cannula means relative to said needle means to a position whereat said distal end of said cannula means covers said sampling means of said needle means to capture the tissue specimen in said sampling means of said needle means; and means for adjusting the degree of exposure of said sampling means relative to said cannula means when said needle means is released from said predetermined position to move to said sampling position, said means for adjusting including spacer means mounted on said sleeve and adjustable for adjusting the length of said sleeve and the extent of forward movement of said needle means relative to said cannula means during operation of the apparatus.

9. The apparatus of claim 8 wherein the forward end of said sleeve is threaded and said spacer means is threadedly received on the forward end of said sleeve.

* * * * *

UNITED STATES PATENT AND TRADEMARK OFFICE
CERTIFICATE OF CORRECTION

PATENT NO. : 5,172,702
DATED      : December 22, 1992
INVENTOR(S) : Harold G. Leigh, David L. O'Dell and Hugh A. Bourassa It is certified that error appears in the above-identified patent and that said Letters Patent is hereby corrected as shown below:

Column 3, line 42  after back insert -- end --

Column 3, line 54  delete "summa" and insert -- summary --

Column 8, line 31  delete "te" and insert -- the --

Signed and Sealed this

Twenty-third Day of November, 1993

Attest:

BRUCE LEHMAN

Attesting Officer    Commissioner of Patents and Trademarks